United States Patent [19]

Yamanishi et al.

[11] Patent Number: 4,910,134

[45] Date of Patent: Mar. 20, 1990

[54] ASCORBIC ACID DECOMPOSING METHOD

[75] Inventors: Kazuhiko Yamanishi, Tokyo; Toshiro Hanada, Saitama, both of Japan

[73] Assignee: Wako Pure Chemical Industries Ltd, Osaka, Japan

[21] Appl. No.: 6,223

[22] Filed: Jan. 23, 1987

Related U.S. Application Data

[63] Continuation of Ser. No. 674,826, Nov. 14, 1984, abandoned.

[30] Foreign Application Priority Data

Jun. 13, 1983 [JP]  Japan .................................. 58-105602
Jun. 12, 1984 [WO]  PCT Int'l Appl. ... PCT/JP84/00306

[51] Int. Cl.$^4$ .......................... C12Q 1/62; C12Q 1/60; C12Q 1/54; C12Q 1/26; C12Q 1/28
[52] U.S. Cl. ........................................ 435/10; 435/11; 435/14; 435/25; 435/28
[58] Field of Search .................... 435/25, 28, 10, 11, 435/14; 436/66, 93, 175, 135, 825, 903

[56] References Cited

U.S. PATENT DOCUMENTS

| | | | |
|---|---|---|---|
| 3,411,887 | 11/1968 | Ku ............................................ | 435/25 |
| 4,228,240 | 10/1980 | Dawson et al. ........................ | 435/188 |
| 4,439,527 | 3/1984 | Pakebusch et al. ................... | 436/904 |
| 4,503,144 | 5/1985 | Deeg et al. ............................. | 435/28 |
| 4,521,511 | 4/1985 | Stout ....................................... | 435/28 |
| 4,587,220 | 5/1986 | Mayambala-Mwanika et al. ............................................ | 435/28 |
| 4,743,559 | 5/1988 | Koevér et al. ......................... | 436/175 |

OTHER PUBLICATIONS

Weissberger et al. "Oxidation Processes. XVII. The Autoxidation of Ascorbic Acid in the Presence of Copper." J. Am. Chem. Soc., vol. 66, pp. 700–705.
Barron et al, "J. Biol. Chem.," 112 (1936) pp. 625–640.
White-Stevens, "Clin. Chem.," 28:4 (1982) pp. 578–588.
Gochman et al, Clin. Chem., 18(9):943–950 (1972).
Research Disclosure, (Aug. 1977), p. 19.

Primary Examiner—Esther M. Kepplinger
Attorney, Agent, or Firm—Cushman, Darby & Cushman

[57]  ABSTRACT

A method for decomposing ascorbic acid in a sample is descirbed wherein in the method water and dehydroascorbic acid are produced without generation of hydrogen peroxide characterized in that the decomposition is conducted in the presence of copper ion, peroxidase and at least one other compound selected from the group consisting of:
4-aminoantipyrine,
3-methyl-2-benzothiazolinonehydrazone,
2,2'-azinobis(3-ethylbenzothiazoline-6 sulphonic acid),
a triphenyl methane type leuco compound,
a phenol comound.
an aniline compound, and
a naphthol compound.

9 Claims, 1 Drawing Sheet

ASCORBIC ACID DECOMPOSING METHOD

RELATED APPLICATIONS

This is a continuation application of application Ser. No. 06/674,826 filed Nov. 14, 1986 and now abandoned.

TECHNICAL FIELD

The present invention relates to a novel method of decomposing ascorbic acid in a sample.

BACKGROUND TECHNIQUE

Ascorbic acid is a publicly known reducing substance as vitamin C, and it is well known that when it is coexistent in a sample to be examined, for instance, a component in a body fluid, a positive or negative measuring error is produced by the reducing property of ascorbic acid in quantitative measurement of an intended component in the sample to be examined by utilizing oxidation-reduction reaction.

Meanwhile, there have been reported as the ascorbic acid decomposing methods (1) a method using ascorbate oxidase (Japanese Patent Publication No. 39,198/1981), (2) a method using iodic acid or a salt thereof, (3) a method using periodic acid or the like or a salt thereof (Japanese Patent Laid-Open No. 109,595/1981; Japanese Patent Laid-Open No. 151,358/1981; Japanese Patent Laid-Open No. 107,161/1981) and so on.

However, the above method (1) using ascorbate oxidase has the defects that since ascorbate oxidase is an enzyme, it has a problem peculiar to the enzymes, that is, a poor thermal stability and a poor storage stability. In addition, although it is strongly demanded to develop a color through one step reaction by using a one liquid type reagent in which necessary reagents are all present in a single liquid or reagents to be gathered in a single liquid in a measuring system in the case of the quantitative measurement of the intended component in the sample to be examined by utilizing the oxidation-reduction reaction, when the above method (1) is applied to this one step reaction, unless a large amount of ascorbate oxidase is used, an oxidase first acts upon a substrate as the intended component in the measurement, so that producing reaction of hydrogen peroxide with the oxidase unfavorably proceeds preferentially when ascorbic acid to be decomposed is still present. There is also a problem that when ascorbate oxidase is used in a large amount to avoid this, it is uneconomical due to its high price.

Further, the method using iodic acid or the salt thereof and the method using periodic acid or the like or the salt thereof have the problem that the enzymatic activity of the oxidase and the like is interfered by the oxidizing action of the oxidizing agent in some case. Moreover, even if the oxidase acts upon the substrate without its enzymatic activity being interfered to quantitatively generate hydrogen peroxide, there has not been developed such an oxidizable coloring reagent up to now that an appropriate pH of coloring of the oxidizable coloring reagent for leading the generated hydrogen peroxide to a coloring system is in coincidence with an appropriate pH at which ascorbic acid is decomposed with iodic acid or the salt thereof or periodic acid or the like or the salt thereof, so that the above method (2) or (3) can not be applied to the one step reaction. Furthermore, since when such periodic acids or the like or the salt thereof is used, a decomposing agent such as an alcohol or an aldehydes is required to decompose an excessive amount of periodic acid or the like or the salt thereof the above method (3) can not be applied to the one step reaction from this respect.

On the other hand, the reaction in which ascorbic acid is oxidized in the presence of divalent copper ion ($Cu^{2+}$ ion) to produce dehydroascorbic acid and $H_2O_2$ has been formerly known (See E. S. GUZMAN BARRON, R. H. DeMEIO, AND FRIEDRICH KLEMPERER, J. Biol. Chem. 112, 625–640 (1936)). However, this is a reaction in which $H_2O_2$ is produced together with dehydroascorbic acid, and in order to apply this decomposition reaction to a reaction in which $H_2O_2$ produced by acting an oxidase upon a substrate is measured to quantitatively analyze the intended component in a sample to be examined, the amounts of $H_2O_2$ produced in both of these reactions must be able to be discerned and detected, but needless to say, such is substantially impossible.

Therefore, it has not been hit upon at all to try to apply such a reaction that ascorbic acid is decomposed through oxidation in the presence of $Cu^{2+}$ ion to the reaction in which $H_2O_2$ produced by acting the oxidase upon the substrate is measured to to quantitatively analyze the intended component in the sample to be examined.

It is an object of the present invention to provide a method of decomposing ascorbic acid without producing hydrogen peroxide.

Further, it is another object of the present invention to provide a decomposition method which can effectively remove the effects of ascorbic acid contained in a reaction system in the quantitative measurement of a component in a body fluid in which $H_2O_2$ is produced by acting an oxidase upon a substrate, and the thus produced $H_2O_2$ is quantitatively measured.

It is still another object of the present invention to provide a method of decomposing ascorbic acid, in which the decomposition of ascorbic acid and a reaction in which a sample to be examined is subjected to enzyme reaction to be led to a coloring system can be carried out by one step.

DISCLOSURE OF THE INVENTION

Under these circumstances, the present inventors have found during strenuous studies upon the decomposition reaction of ascorbic acid in the presence of copper ion that there exists a reaction in which ascorbic acid is oxidized in the presence of copper ion to produce dehydroascorbic acid and $H_2O$; such a decomposition reaction needs peroxidase and one or more kinds of compounds selected from a group consisting of (1) 4-aminoantipyrine, (2) 3-methyl-2-benzothiazolinonehydrazone, (3) 2,2'-azinobis (3-ethylbenzothiazoline-6-sulfonic acid), (4) triphenyl methane type leuco compound, (5) phenol compound, (6) aniline compound, and (7) naphthol compound in addition to the copper ion; and this method is applicable to the method of quantitatively measuring the component in the body fluid in which $H_2O_2$ is produced by acting the oxidase upon the substrate, and the thus produced $H_2O_2$ is measured to quantitatively analyze the intended component in the sample to be examined, and have accordingly accomplished the present invention.

That is, the present invention is a method of decomposing ascorbic acid, which is characterized by coexisting monovalent or divalent copper ion, peroxidase, and one or more kinds of compounds selected from the group consisting of the following (1)–(7).
(1) 4-aminoantipyrine (4-AAP)
(2) 3-methyl-2-benzothiazolinonehydrazone (MBTH)
(3) 2,2'-azinobis(3-ethylbenzothiazoline-6-sulfonic acid) (ABTS)
(4) triphenyl methane type leuco compound
(5) phenol compound
(6) aniline compound
(7) naphthol compound The reaction of the invention proceeds according to the following formula:

$$\text{ascorbic acid} + \tfrac{1}{2}O_2 \xrightarrow[\text{one or more kinds of compounds (1)-(7)}]{Cu^{2+},\ \text{peroxidase}} \text{dehydroascorbic acid} + H_2O$$

Taking into consideration the fact that it has been conventionally thought fixedly that if $Cu^{2+}$ ion is present in the reaction system of the oxidation decomposition reaction of ascorbic acid, a substance which is produced together with dehydroascorbic acid is $H_2O_2$, it must be said that it is inconceivable and unexpectable that there exists a reaction in which $H_2O$ is produced with the production of dehydroacorbic acid in the oxidation decomposition reaction of ascorbic acid in the presence of the $Cu^{2+}$ ion.

Although it has been conventionally considered that the copper ion which decomposes ascorbic acid is divalent copper ion, the present inventors have discovered that $Cu^{2+}$ is present in a form of $Cu^{+}$ through being reduced in the case of coexistence of a reducing substance such as 4-aminoantipyrine or 3-methyl-2-benzothiazolinonehydrazone, and the copper ion decomposes ascorbic acid to be converted to dehydroascorbic acid and $H_2O$. That is, the present inventors have first found that the copper ion which decomposes ascorbic acid is not necessarily limited to the divalent copper ion, and that the monovalent copper ion exhibits similar effect.

The novel reagent composition according to the present invention which comprises the monovalent or divalent copper ion, peroxidase and one or more kinds of compounds selected from the group consisting of (1) 4-aminoantipyrine, (2) 3-methyl-2-benzothiazolinonehydrazone, (3) 2,2'-azinobis(3-ethylbenzothiazoline-6-sulfonic acid), (4) triphenyl methane type leuco compound (5) phenol compound, (6) aniline compound and (7) naphthol compound has the effect that the composition acts upon bilirubin which belongs to the same reducing substances as ascorbic acid to make its reducing activity lost. Therefore, when the method according to the present invention is applied to a reaction in which an oxidative substance such as $H_2O_2$ is measured to quantitatively analyze the intended substance, that is, an oxidation-reduction reaction (redox reaction) for quantitatively measuring the intended component, the interference of the reducing substance such as ascorbic acid or bilirubin present in the reaction system can be effectively avoided, so that the intended component can be quantitatively measured with accuracy without being adversely affected by such interference.

The copper ion necessary for the decomposition of ascorbic acid without being accompanied by the production of $H_2O_2$ in the present invention may be monovalent copper ion or divalent copper ion, and the divalent copper ion is more preferable. Even when the divalent copper ion is used, it may be present in the monovalent ion state in the reaction system due to the strength of the reducing power of the reagents (1)–(7) combinationingly used, or may be present as they are.

According to the present invention, in 4-aminoantipyrine, 3-methyl-2-benzothiazolinonehydrazone, 2,2'-azinobis(3-ethylbenzothiazoline-6-sulfonic acid), triphenyl methane type leuco compound, phenol compound, aniline compound and naphthol compound, which are used together with the monovalent or divalent copper ion and peroxidase for decomposing ascorbic acid, as specific examples of the triphenyl methane type leuco compound, mention may be made of the conventionally known leucomalachite green, leucocrystal violet and the like as well as bis(p-diethylaminophenyl)-2-sulfophenyl methane, bis(p-diethylaminophenyl)-4-sulfopropoxyphenyl methane sodium salt, bis(p-diethylaminophenyl)-3,4-disulfopropoxyphenyl methane disodium salt (hereinafter referred to briefly as BSdiproPM) and the like which have been recently developed.

As specific examples of the phenol compound, mention may be made of phenol, p-chlorophenol, 2,4-dichlorophenol, p-bromophenol, o-chlorophenol, m-cholorophenol and the like. As the aniline compound, aniline, N,N-dimethylaniline, N,N-diethylaniline, N,N-diethyl-m-toluidine, 3-methyl-N-ethyl-N-($\beta$-hydroxyethyl)aniline, N-ethyl-N-(2-hydroxy-3-sulfopropyl)-m-toluidine, 3,5-dimethyl-N-ethyl-N-(2-hydroxy-3-sulfopropyl)aniline, 3,5-dimethoxy-N-ethyl(2-hydroxy-3-sulfopropyl)aniline and the like.

Further, as the naphthol compounds, mention may be made of 1-naphthol, 1-naphthol-2-sulfonic acid, 1-naphthol-2-carboxylic acid, 1-naphthol-8-sulfonic acid, 1-naphthol-3-sulfonic acid, 1-naphthol-5-sulfonic acid and the like.

The decomposition reaction of the reducing substance in the present invention is ordinarily carried out in a solution.

The concentration of $Cu^{+}$ or $Cu^{2+}$ in such a solution is set, for instance, at 0.001–1 m mol/l, and its pH is, for instance, at 6.0–8.5. As the buffers solution for maintaining the solution at such a pH, use may be made of, for instance, phosphate buffer solution, tris(hydroxymethyl)aminomethane salt buffer solution, Good buffer solution and the like which are widely employed. As the preferred example thereof, mention may be made of 0.001–2M phosphate buffer solution.

The compound which gives $Cu^{+}$ or $Cu^{2+}$ ion in such a solution, mention may be made of a water-soluble copper compound, for example, a water-soluble inorganic copper salt such as copper salfate, cupric chloride, cuprous chloride, copper nitride, cupric bromide, cuprous bromide, cupric phosphate, a water-soluble organic copper salt such as copper tartrate, copper citrate, copper acetate and the like.

The concentration of peroxidase used in the present invention is ordinarily 20–5,000 U/dl, and preferably 50–2,000 U/dl.

The concentration of 4-aminoantipyrine (4-AAP) is ordinarily 0.001–0.05%, preferably 0.003–0.03%.

The concentration of 3-methyl-2-benzothiazolinonehydrazone (MBTH) is ordinarily 0.0005–0.2%, preferably 0.001–0.05%.

The concentration of 2,2'-azinobis(3-ethylbenzothiazoline-6-sulfonic acid) (ABTS) is ordinarily 0.002–0.4%, preferably 0.02–0.2%.

The concentration of triphenyl methane type leuco compound is ordinarily 0.005–0.5 m mol/l, preferably 0.03–0.3 m mol/l.

The concentration of phenol compound, aniline compound or naphthol compound is ordinarily 0.01–0.5%, preferably 0.03–0.3%.

The method of decomposing the reducing substance according to the present invention is also used in a test paper in which all reagents are present in a dried state in an absorbing carrier or film.

When the method according to the present invention is performed as a pretreatment prior to the measurement of the component in the body fluid, ascorbic acid and bilirubin are rapidly oxidized, and their interfering action disapears.

A measuring method which is particularly effective when the method of decomposing the reducing substance according to the present invention is applied is a measuring method in which a sample to be examine is a body fluid and an intended component to be quantitatively measured is a body fluid component, and typical example as the reaction of quantitatively measuring the intended component is an enzyme reaction in which the intended component in the quantitative measurement is a substrate or enzyme, and the enzyme is an enzyme to cause $H_2O_2$ to be produced when the enzyme acts upon the substrate. As examples of such a reaction, mention may be made of systems in which the substrate is glucose, cholesterol, glycerol, glycerol phosphate, choline, acylCoA, pyruvic acid, uric acid, xanthine or lactic acid, and the oxidase acting upon these substrate is glucose oxidase, cholesterol oxidase, glycerol oxidase, glycerol phosphate oxidase, choline oxidase, acylCoA oxidase, pyruvic acid oxidase, uricase, xanthine oxidase or lactic acid oxidase.

When $H_2O_2$ produced in such a reaction is measured to analyze the intended component, it is a common practice that an oxidizable coloring reagent which is colored through being oxidized in the presence of $H_2O_2$ and peroxidase is used, and the color of the reagent developed by the $H_2O_2$ produced is measured to quantitatively analyze the intended component.

As the oxidizable coloring reagent used for this purpose, mention may be made, singly or in a combined reagent state, of a combined reagent of 4-aminoantipyrine (4-AAP) and a phenol compound, a combined reagent of 4-aminoantipyrine (4AAP) and an aniline compound, a combined reagent of 4-aminoantipyrine (4-AAP) and a naphthol compound, a combined reagent of 3-methyl-2-benzothiazolinonehydrazone (MBTH) and an aniline compound, 2,2'-azinobis(3-ethylbenzothiazoline-6-sulfonic acid) (ABTS), triphenyl methane type leuco compound, and the like which are the same as the reagents necessary for decomposing ascorbic acid without producing $H_2O_2$ in the present invention. As specific examples of the triphenyl methane type leuco compound, the phenol compound, the aniline compound, the naphthol compound and the like, the triphenyl methane type leuco compound, the phenol compound, the aniline compound, the naphthol compound which are the same as mentioned before to be used in the present invention may be mentioned.

Examples of the quantitatively measuring reagent in the method of quantitatively measuring the body fluid component in which $H_2O_2$ is produced by acting the oxidase upon the substrate to which the present invention is applied, and thus produced $H_2O_2$ is measured to quantitatively analyze the intended component in the sample to be examined may be recited as follows:

(1) In case of measurement of glucose, a reagent which contains peroxidase, glucose oxidase, 4-aminoantipyrine, phenol or N,N-diethylxylidine and a buffer.

(2) In case of measurement of uric acid, a reagent which contains peroxidase, uricase, N-ethyl-N-($\beta$-hydroxyethyl)-m-toluidine, 4-aminoantipyrine and a buffer.

(3) In case of measurement of cholesterol, a reagent which contains peroxidase, cholesterol ester hydrolase, cholesterol oxidase, 4-aminoantipyrine, phenol or N-ethyl-N-($\beta$-hydroxyethyl)-m-toluidine and a buffer.

(4) In case of measurement of triglyceride, a reagent which contains peroxidase, lipoprotein lipase, glycerol kinase, glycerol-3-phosphate oxidase, 4-aminoantipyrine, p-chlorophenol or N-ethyl-N-($\beta$-hydroxyethyl)-m-toluidine and a buffer.

(5) In case of measurement of phospholipid, a reagent which contains peroxidase, phospholipase D, choline oxidase, 4-aminoantipyrine, phenol or N-ethyl-N-($\beta$-hydroxyethyl)-m-toluidine and a buffer.

(6) In case of measurement of acylCoA, a reagent which contains peroxidase, acylCoA oxidase, 4-aminoantipyrine, p-chlorophenol or N-ethyl-N-($\beta$-hydroxyethyl)-m-toluidine and a buffer.

(7) In case of measurement of pyruvic acid, a reagent which contains peroxidase, pyruvate oxidase, flavin adenine dinucleotide, thiamine pyrophosphate, 4-aminoantipyrine, p-chlorophenol or N-ethyl-N-($\beta$-hydroxyethyl)-m-toluidine and a buffer.

(8) In case of measurement of glycerol, a reagent which contains peroxidase, glycerol oxidase, 4-aminoantipyrine, p-chlorophenol or N-ethyl-N-($\beta$-hydroxyethyl)-m-toluidine and a buffer.

(9) In case of measurement of choline, a reagent which contains peroxidase, choline oxidase, 4-aminoantipyrine, phenol or N-ethyl-N-($\beta$-hydroxyethyl)-m-toluidine and a buffer.

(10) In case of measurement of glycerol-3-phosphate, a reagent which contains peroxidase, glycerol-3-phosphate oxidase, 4-aminoantipyrine, p-chlorophenol or N-ethyl-N-($\beta$-hydroxyethyl)-m-toluidine and a buffer.

(11) In case of measurement of uric acid, a reagent which contains peroxidase, uricase, 2,2'-azinobis(3-ethylbenzothiazoline-6-sulfonic acid) and a buffer.

When the ascorbic acid-decomposing method and the decomposing reagent according to the present invention are applied to the method of quantitatively measuring the body fluid component by using the above-mentioned quantitatively measuring reagent, since it is possible to effectively avoid the interference of a reducing substance such as ascorbic acid or bilirubin coexisting in the reaction system in which the oxidizing substance or a reducing substance is measured to quantitatively analyzing the intended component in the case that the reaction is done in one step using one liquid type reagent in which necessary reagents are all present in a single liquid or reagents which are gathered into a single liquid in the measuring system, which is most required in the measurement of the intended component in the sample to be examined by using the oxidation-reduction reaction (redox reaction), the intended component can be quantitatively measured with accuracy without being adversely affected by such interference.

For instance, in order to quantitatively measure free cholesterol in serum, when $CuSO_4 \cdot 5H_2O$, 4-AAP, a phenol compound, an aniline compound or a naphthol compound, peroxidase, cholesterol oxidase and a surface active agent are added to be at the concentrations of 0.001–1 m mol/l, 0.003–0.03%, 0.03–0.3%, 50–2,000 U/dl, 5–100 U/dl and 0.05–0.2% respectively, and a buffer solution dissolving these compounds is used as measuring reagent, the interference of the reducing substance such as ascorbic acid and bilirubin present in the serum can be effectively avoided to be able to measure the value of free cholesterol with more accuracy.

BEST MODE FOR PRACTICING THE INVENTION

Ascorbic Acid Decomposition:

Example 1

Measuring Reagent (1) First reagent:

$CuSO_4 \cdot 5H_2O$, peroxidase (POD), phenol, 1-naphthol-2-sulfonic acid, and 4-AAP are singly or in a combination of more than one thereof into 0.05M phosphate buffer solution (pH=7.0) in the composition shown in following Table 1, provided that $CuSO_4 \cdot 5H_2O$, POD, phenol, and 1-naphthol-2-sulfonic acid were adjusted to be at concentrations of 0.003%, 300 U/dl, 0.1%, and 0.01% respectively.

(2) Second reagent (coloring reagent):

A coloring reagent solution was prepared by dissolving POD, phenol, and 4-AAP into 0.05M phosphate buffer solution (pH=7.0) to be at concentrations of 300 U/dl, 0.1%, and 0.01% respectively.

When the reagent solution containing 1-naphthol-2-sulfonic acid was used as the first reagent solution, the reagent solution in which POD, 1-naphthol-2-sulfonic acid, and 4-AAP are dissolved into 0.05M phosphate buffer solution (pH=7.0) to be at concentrations of 300 U/dl, 0.1% respectively was used as the second reagent solution (coloring reagent solution).

Measuring Method

After 50 μl of an ascorbic acid solution (100 mg/dl) was sampled, 2 ml of the first reagent solution was added thereto, and was incubated at 37° C. for 3 minutes. Then, 2 ml of the second reagent solution (coloring reagent solution) was added thereto, and was incubated at 37° C. for 5 minutes. An absorbance at a wavelength of 505 nm was measured with reference to a reagent blank as a control. Results where shown in Table 1.

TABLE 1

| Composition in the first reagent solution | Absorbance (OD) |
|---|---|
| $CuSO_4$ | 0.205 |
| $CuSO_4$, POD | 0.164 |
| $CuSO_4$, POD, 4-AAP | 0.000 |

TABLE 1-continued

| Composition in the first reagent solution | Absorbance (OD) |
|---|---|
| $CuSO_4$, POD, phenol | 0.001 |
| $CuSO_4$, POD, 1-naphthol-2-sulfonic acid | 0.001 |
| $CuSO_4$, POD, phenol, 4-AAP | 0.001 |
| $CuSO_4$, POD, 1-naphthol-2-sulfonic acid, 4-AAP | 0.001 |
| $CuSO_4$, 4-AAP | 0.206 |
| $CuSO_4$, phenol | 0.203 |
| $CuSO_4$, 1-naphthol-2-sulfonic acid | 0.202 |

Note: When $H_2O_2$ is produced through decomposition of ascorbic acid, 4-AAP and phenol or 4-AAP and 1-naphthol-2-sulfonic acid in the system are oxidized with the thus produced $H_2O_2$ and an absorption appears in the vicinity of a wavelength of 505 nm.

It is seen from this experiment that when 4-AAP, phenol, 1-naphthol-2-sulfonic acid, phenol and 4-AAP, or 4-AAP and 1-naphthol-2-sulfonic acid are coexistent besides copper ion and POD, no production of $H_2O_2$ is recognized. However, it is considered that when any one of 4-AAP, phenol, and 1-naphthol-2-sulfonic acid is coexistent in the first reagent solution besides copper ion and POD, even if $H_2O_2$ is produced, the $H_2O_2$ is removed by POD and 4-AAP, phenol or 1-naphthol-2-sulfonic acid, and thus no $H_2O_2$ is detected from the appearance (since even oxidation produces no great change when viewed from an external appearance in the case of 4-AAP alone, phenol alone, or 1-naphthol-2-sulfonic acid alone; whether or not $H_2O_2$ is produced can not be confirmed in the above experiment). Taking it into account, an experiment was next made to confirm that even in these cases, ascorbic acid is decomposed without being accompanied by the production of $H_2O_2$.

Experiment 2

Measuring Reagent (1) First reagent solution:

$CuSO_4 \cdot 5H_2O$, POD, and 4-AAP (or phenol or 1-naphthol-2-sulfonic acid) were dissolved into 0.05M phosphate buffer solution (pH=7.5) to be at concentrations of 0.003%, 300 , U/dl, and 0.017% respectively (0.01% in the case of phenol or 1-naphthol-2-sulfonic acid).

(2) Second reagent solution (coloring reagent solution):

$NaIO_4$ and phenol(or 4-AAP) were dissolved into 0.05M phosphate buffer solution (pH=7.5) to be at concentrations of 20 mg/dl and 0.1% respectively (0.01% in the case of 4-AAP).

When the reagent solution containing 4-AAP was used as the first reagent solution, the reagent solution containing phenol was used as the second reagent solution, while when the reagent solution containing phenol or 1-naphthol-2-sulfonic acid was used as the first reagent solution, the reagent solution containing 4-AAP was used as the second reagent solution.

Measuring Method

As sample, a solution in which ascorbic acid was dissolved into 0.05M phosphate buffer solution (pH=7.5) at a concentration of 0 mg/dl, 100 mg/dl, or 200 mg/dl (11 m mol/l) or a solution in which $H_2O_2$ was dissolved into 0.05M phosphate buffer solution at a concentration of 0 m mol/l, 5 m mol/l, or 10 m mol/l was used.

100 μl of the sample was sampled, 2 ml of the first reagent liquid was added thereto, and was incubated at 37° C. for 10 minutes. 100 μl of the resulting mixed solution was sampled, 3 ml of the second reagent solution (coloring reagent solution) was added thereto, and was incubated at 37° C. for 5 minutes. Thereafter, an absorbance at a wavelength of 505 nm was measured with reference to a reagent blank as a control. Measured results were shown in Table 2.

TABLE 2

| Sample | Ascorbic acid | | | Sample | $H_2O_2$ | | |
|---|---|---|---|---|---|---|---|
| Sample concentration* | 4-AAP | Phenol | 1-Naphthol-2-sulfonic acid | Sample concentration* | 4-AAP | Phenol | 1-Naphthol-2-sulfonic acid |
| 0(mg/dl) | 0.278 | 0.361 | 0.360 | 0 (m mol/l) | 0.282 | 0.370 | 0.368 |
| 100 | 0.281 | 0.352 | 0.358 | 5 | 0.197 | 0.190 | 0.187 |
| 200 (11 m mol/l) | 0.278 | 0.359 | 0.358 | 10 | 0.123 | 0.092 | 0.090 |

*component other than copper ion and POD in the first reagent solution

From the above, it can be said that since the coexisting 4-AAP, phenol, and 1-naphthol-2-sulfonic acid undergo no change at all in the decomposition of ascorbic acid with copper ion, it can be said that no $H_2O_2$ is produced in this reaction system. On the other hand, when $H_2O_2$ is used as the sample in a substantially equal mole to the ascorbic acid, 4-AAP, phenol, and 1-naphthol-2-sulfonic acid are apparently oxidized with the $H_2O_2$. In the 4-AAP coexisting system, red color developed, while in the phenol system and in the naphthol system, yellowish brown developed. When the remaining concentration of the $H_2O_2$ in the reaction system is measured, it is recognized that the $H_2O_2$ is apparently consumed.

Example 3

Measuring Reagent (1) First reagent solution:

$CuSO_4 \cdot 5H_2O$, POD, 3-methyl-N-ethyl-N-($\beta$-hydroxyethyl)-aniline (MEHA), and 3-methyl-2-benzothiazolinonehydrazone (MBTH) were singly or in a combination of more than one kind thereof dissolved into 0.05M phosphate buffer solution (pH=7.0) at the composition shown in the following Table 3, provided that $CuSO_4 \cdot 5H_2O$, POD, MEHA and MBTH were adjusted to be at concentrations of 0.003%, 300 U/dl, 0.05% and 0.03% respectively.

(2) Second reagent solution (coloring reagent solution):

When the reagent solution containing MEHA was used as the first reagent solution, a solution in which POD and 4-AAP were dissolved into 0.05M phosphate buffer solution (pH=7.0) to be at concentrations of 300 U/dl and 0.1% respectively was used as the second reagent solution (coloring reagent solution), while when the reagent solution containing MBTH was used as the first reagent solution, a solution in which POD and MEHA were dissolved into 0.05M phosphate buffer solution (pH=7.0) to be at concentrations of 300 U/dl and 0.02% respectively was used as the second reagent solution (coloring reagent solution). When neither MEHA nor MBTH were contained in the first reagent solution, a solution in which POD, MEHA and 4-AAP were dissolved into 0.05M phosphate buffer solution (pH=7.0) to be at concentrations of 300 U/dl, 0.05% and 0.01% respectively was used as the second reagent solution (coloring reagent solution).

Measuring Method

50μl of an ascorbic solution (100 mg/dl) was sampled, 2 ml of the first reagent solution was added thereto, and was incubated at 37° C. for 5 minutes. Then, 2 ml of the second reagent solution was added, and was incubated at 37° C. for 5 minutes. Thereafter, an absorbance at a wavelength of 550 nm was measured with reference to a reagent blank as a control. Measured results were shown in Table 3.

TABLE 3

| Composition in the first reagent solution | Absorbance (OD) |
|---|---|
| $CuSO_4$ | 0.434 |
| $CuSO_4$, POD | 0.314 |
| $CuSO_4$, POD, MEHA | −0.001 |
| $CuSO_4$, POD, MBTH | 0.004 |
| $CuSO_4$, MEHA | 0.416 |
| $CuSO_4$, MBTH | 0.073 |

It seems from this experiment that when MEHA or MBTH besides copper ion and POD is coexistent in the first reagent solution, no $H_2O_2$ is produced when viewed from the external appearance. However, whether or not ascorbic acid is actually decomposed without being accompanied by the production of $H_2O_2$ can not be known from this experiment, and therefore, the following experiment was made to confirm this.

Example 4

Measuring Reagent (1) First reagent solution:

$CuSO_4 \cdot 5H_2O$, POD and MEHA (or MBTH) were dissolved into 0.05M phosphate buffer solution (pH=7.5) to be at concentrations of 0.003%, 300 U/dl and 0.019% (0.025% in the case of MBTH).

(2) Second reagent solution (coloring reagent solution):

$NaIO_4$, and 4-AAP (or MEHA) were dissolved into 0.05M phosphate buffer solution (pH=7.5) to be at concentrations of 20 mg/dl and 0.01% respectively (0.01% in the case of MEHA).

When the reagent solution containing MEHA was used as the first reagent solution, the reagent solution containing 4-AAP was used as the second reagent solution, while when the reagent solution containing MBTH was used as the first reagent solution, the reagent solution containing MEHA was used as the second reagent solution.

Measuring Method

As sample, a solution in which ascorbic acid was dissolved into 0.05M phosphate buffer solution (pH=7.5) to be at a concentration of 0 mg/dl, 100 mg/dl or 200 mg/dl (11 m mol/l), or a solution in which $H_2O_2$ was dissolved into 0.05M phosphate buffer solution to be at a concentration of 0 m mol/l, 5 m mol/l or 10 m mol/l was used.

100 μl of a sample was sampled, 2 ml of the first reagent solution was added thereto, and was incubated at 37° C. for 10 minutes. 100 μl of the resulting mixed solution was sampled, 3 ml of the second reagent solution was added thereto, and was incubated at 37° C. for 5 minutes. Thereafter, an absorbance at a wavelength of 550 nm was measured with reference to a reagent blank as a control. Measured results were shown in Table 4.

TABLE 4

| Sample Sample Concentration* | Ascorbic acid MEHA | MBTH | Sample Sample Concentration* | $H_2O_2$ MEHA | MBTH |
|---|---|---|---|---|---|
| 0 (mg/dl) | 0.900 | 0.539 | 0 (m mol/l) | 0.920 | 0.554 |
| 100 | 0.896 | 0.538 | 5 | 0.472 | 0.285 |
| 200 (11 m mol/l) | 0.898 | 0.536 | 10 | 0.230 | 0.138 |

*Component other than copper ion and POD in the first reagent solution

From the above, it can be said that since the coexisting MEHA and MBTH are not changed at all in the decomposition of ascorbic acid with copper ion, it can be said that no $H_2O_2$ is produced in this reaction system. On the other hand, when $H_2O_2$ in a substantially equal mol to the ascorbic acid is used as a sample, MEHA and MBTH are apparently oxidized with the $H_2O_2$, and it is seen through the measurement of the remaining $H_2O_2$ that the $H_2O_2$ is actually consumed.

Example 5

Measuring Reagent (a) A solution in which $CuSO_4 \cdot 5H_2O$, POD and ABTS were dissolved into 0.05M phosphate buffer (pH=7.0) at concentrations of 0.03%, 300 U/dl and 0.1% respectively.

(b) A solution in which $CuSO_4 \cdot 5H_2O$, POD and bis(p-diethylaminophenyl)-3,4-disulfopropoxyphenyl methane disodium salt (hereinafter abbreviated as BSdiproPM) were dissolved into 0.05M phosphate buffer solution (pH=7.0) at concentrations of 0.003%, 300 U/dl, and 0.05 mM respectively.

Measuring Method

50 μl of an ascorbic acid solution (100 mg/dl) was sampled, the measuring reagent solution (a) or (b) was added thereto, and was incubated at 37° C. for 3 minutes. Then, an absorbance at a wavelength of 660 nm or 620 nm was measured with reference to a reagent blank as a control. Measured results were shown in Table 5.

TABLE 5

| Composition in the measuring reagent solution | Absorbance (OD) |
|---|---|
| $CuSO_4$, POD, ABTS | 0.000 |
| $CuSO_4$, POD, BSdiproPM | 0.000 |

It is seen from this experiment that when the copper ion, POD and ABTS are coexistent, and when the copper ion, POD and triphenyl methane type leuco coloring matter are coexistent, ascorbic acid is decomposed without being accompanied by the production of $H_2O_2$.

Next, in order to confirm whether the copper ion is present in a form of divalent or monovalent form in the reaction system of the present invention, an experiment was made by using bathocuproine disulfonic acid, 2 Na salt as a coloring reagent of $Cu^+$.

Example 6

Measuring Sample $CuSO_4 \cdot H_2O$, POD, phenol, 1-naphthol-2-sulforic acid, 4-AAP, ABTS, BSdiproPM, and MBTH were singly or in a combination of more than one kind thereof dissolved into 0.05 M phosphate (pH=7.0), provided that $CuSO_4 \cdot 5H_2O$, POD, phenol, 1-naphthol-2-sulfonic acid, 4-AAP, ABTS, BSdiproPM and MBTH were adjusted to be at concentrations of 0.03%, 300 U/dl, 0.1%, 0.1%, 0.01%, 0.1%, 0.1 m mol/l, and 0.1% respectively.

Coloring Reagent Solution

Bathocuproine disulfonic acid, 2 Na salt was dissolved into 0.5M phosphate buffer solution (pH=4.4) to be at a concentration of 10 mg/dl.

Measuring Method

To 0.5 ml of a measuring sample of each of various compositions was added 2 ml of a coloring reagent solution, and an absorbance at a wavelength of 480 nm was measured, from which the concentration of $Cu^+$ in the measuring sample was calculated. Further, 20 mg of ascorbic acid was added to this reaction solution, and an absorbance at a wavelength of 480 nm was measured again, from which the concentration of $Cu^+$ in the measuring sample was calculated. Measured results were shown in Table 6.

TABLE 6

| Composition in the measuring sample | $Cu^+$ concentration (μ/dl) Before Ascorbic acid addition | After Ascorbic acid additon |
|---|---|---|
| $CuSO_4$ | 11 | 756 |
| $CuSO_4$, POD | 7 | 776 |
| $CuSO_4$, POD, 4-AAP | 746 | 734 |
| $CuSO_4$, POD, phenol | 5 | 753 |
| $CuSO_4$, POD, 4-AAP, phenol | 738 | 762 |
| $CuSO_4$, 4-AAP | 763 | 781 |
| $CuSO_4$, phenol | 6 | 758 |
| $CuSO_4$, 4-AAP, phenol | 752 | 753 |
| $CuSO_4$, 1-naphthol-2-sulfonic acid | 5 | 760 |
| $CuSO_4$, ABTS | —* | 762 |
| $CuSO_4$, BSdiproPM | 12 | 767 |
| $CuSO_4$, MBTH | 743 | 758 |

*Since the reaction solution becomes yellowish green, discrimination is impossible. However, when 4-AAP was added to this system, it became yellowish brown. Thus, it was confirmed that $Cu^{2+}$ was changed to $Cu^+$, which was reacted with bathocuproine disulfonic acid, 2 Na salt. Accordingly, it is seen that $Cu+$ is not produced in the case of ABTS and $Cu^{2+}$.

It is seen from the above experiment that when phenol, 1-naphthol-2-sulfonic acid, ABTS or BSdiproPM is coexistent, divalent Cu ion is present as it is, while when 4-AAP or MBTH is coexistent, it is present as a monovalent copper ion.

Decomposition of ascorbic acid or bilirubin in a measuring system of body fluid component

Example 7

Measurement of Total Cholesterol in Serum

Measuring Reagent

Copper sulfate, phenol, 4-aminoantipyrine, peroxidase (POD), cholesterol ester hydrolase, cholesterol oxidase and Rochelle salt and Triton X-100 are dissolved into 0.05M phosphate buffer solution (pH=7.5) to be at concentrations of 0.12 m mol/l, 0.1%, 0.01%, 600 U/dl, 30 U/dl, 15 U/dl, 0.5%, and 0.1% respectively.

Measuring Method

A serum solution in which ascorbic acid was added to 100 ml of serum in an amount of 0, 5, 10, 20, 30, 60, 80 and 100 mg/dl was used as a sample solution.

20 µl of the sample solution was sampled, 3 ml of the measuring reagent was added thereto, and was incubated at 37° C. for 10 minutes. Thereafter, an absorbance at 505 nm was measured with reference to a reagent blank as a control.

Figure 1:
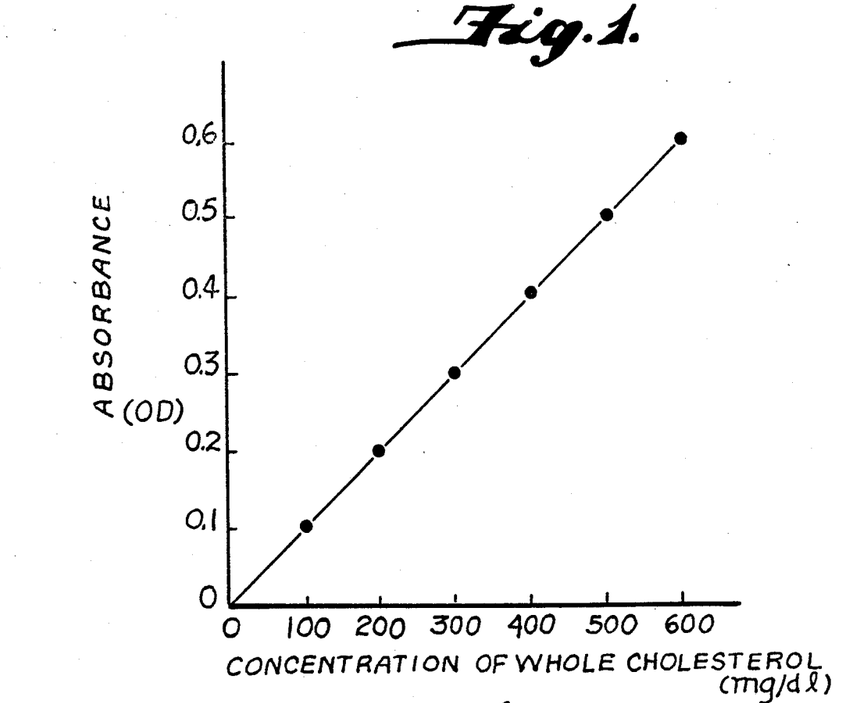
FIG. 1 is a calibration curve obtained in Example 7, in which absorbances (OD) obtained with respect to the concentration (mg/dl) of total cholesterol in an abscissa are plotted along an ordinate, and the plotted points are connected together.

The concentration of the total cholesterol in the sample was calculated from a separately prepared calibration curve (FIG. 1). Measured results were shown in Table 7.

Comparative Example 1

Measuring Reagent

Same as the measuring reagent in Example 7 except for CuSO$_4$·5H$_2$O being excluded therefrom

Measuring Method

The total cholesterol was measured by using the same sample solution as in Example 7 according to the measuring method in Example 7. Measured results were shown in Table 7.

Reference Example 1

Measuring Reagent

Same as the measuring reagent in Example 7 except that AOD is added to be at a concentration of 100 U/dl instead of CuSO$_4$·5H$_2$O.

Measuring Method

The total cholesterol was measured by using the same sample solution as in Example 7 according to the measuring method in Example 7. Measured results were shown in Table 7.

TABLE 7

| Added amount of ascorbic acid (mg/dl) | Total cholesterol concentration (mg/dl) | | |
|---|---|---|---|
| | Example 7 | Comparative Example 1 | Reference Example 1 |
| 0 | 243 (100) | 240 (100) | 241 (100) |
| 5 | 245 (100.8) | 225 (93.8) | 241 (100) |
| 10 | 240 (98.8) | 210 (87.5) | 240 (99.6) |
| 20 | 241 (99.2) | 187 (77.9) | 235 (97.5) |
| 30 | 233 (95.9) | 163 (67.9) | 230 (95.4) |
| 60 | 178 (73.3) | 88 (36.7) | 180 (74.7) |
| 80 | 158 (65.0) | 51 (21.3) | 149 (61.8) |
| 100 | 140 (57.6) | 6 (2.5) | 139 (57.7) |

Note: Figures in parentheses mean recovery rates (%) of cholesterol

As shown in Table 7, when up to 20 mg/dl of ascorbic acid is coexistent in Example 7 in which the copper ion, POD, phenol, and 4-AAP are coexistent, no influence is observed upon the values of the total cholesterol, while when even 5 mg/dl of ascorbic acid is coexistent in Comparative Example 1, a negative influence appears.

Further, as shown in FIG. 7, it is understood that the effect of removing the interference of ascorbic acid according to the method of the present invention is substantially equal to that of AOD.

Example 8

Measurement of Glucose in Serum

Measuring Reagent

Copper sulfate, phenol, 4-aminoantipyrine, peroxidase, glucose oxidase, mutarotase, and Rochelle salt were dissolved into 0.05M phosphate buffer solution (pH=7.0) to be at concentrations of 0.2 m mol/l, 0.1%, 0.01%, 200 U/dl, 4,000 U/dl, 10 U/dl, and 0.5% respectively.

Measuring Method

A serum solution in which ascorbic acid was added into 100 ml of serum in an amount of 0, 5, 10, 20, 30, 60, 80 or 100 mg/dl was used as a sample solution.

20 µl of the sample solution was taken, 3 ml of the measuring reagent was added thereto, and was incubated at 37° C. for 5 minutes. Thereafter, an absorbance at a wavelength of 505 nm was measured with reference to a reagent blank as a control.

Figure 2:
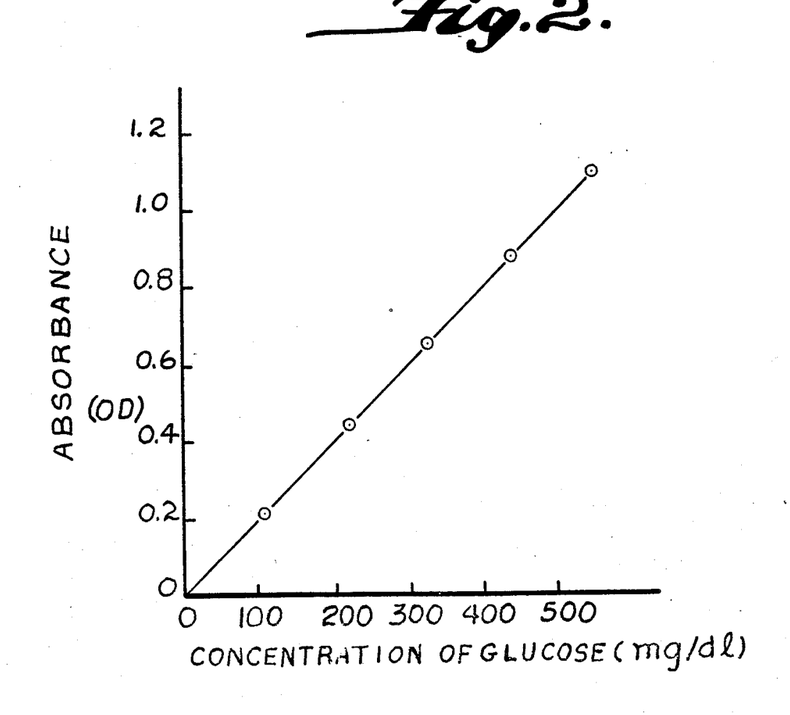
FIG. 2 is a calibration curve obtained in Example 8, in which absorbances (OD) obtained with respect to the concentration (mg/dl) of glucose in an abscissa are plotted along an ordinate, and the plotted points are connected together.

The concentration of the glucose is determined from a separately prepared calibration curve (FIG. 2). Measured results were shown in Table 8.

Comparative Example 2

Measuring Reagent

Same as the measuring reagent in Example 8 except for CuSO$_4$·5H$_2$O being excluded therefrom

Measuring Method

Glucose was measured by using the same sample solution as in Example 8 according to the measuring method in Example 8. Measured results were shown in Table 8.

Reference Example 2

Measuring Reagent

Same as the measuring reagent in Example 8 except that AOD is added to be at a concentration of 100 U/dl instead of CuSO$_4$·5H$_2$O

Measuring Method

Glucose was measured by using the same sample solution as in Example 8 according to the measuring method in Example 8. Measured results were shown in Table 8.

TABLE 8

| Added amount of ascorbic acid (mg/dl) | Glucose concentration (mg/dl) | | |
|---|---|---|---|
| | Example 8 | Comparative Example 2 | Reference Example 2 |
| 0 | 154 (100) | 154 (100) | 153 (100) |
| 5 | 155 (100.6) | 149 (96.8) | 154 (100.7) |
| 10 | 154 (100) | 137 (89.6) | 154 (100.7) |
| 20 | 152 (98.7) | 117 (76.0) | 152 (99.3) |
| 30 | 143 (92.9) | 101 (65.6) | 145 (94.8) |
| 60 | 100 (64.9) | 18 (11.7) | 95 (62.1) |
| 80 | 91 (59.1) | 3 (1.9) | 90 (58.8) |

TABLE 8-continued

| Added amount of ascorbic acid (mg/dl) | Glucose concentration (mg/dl) | | |
|---|---|---|---|
| | Example 8 | Comparative Example 2 | Reference Example 2 |
| 100 | 84 (54.5) | 0 (0) | 81 (52.9) |

Note: Figures in the parentheses mean recovery rates (%) of glucose.

As shown in Table 8, when up to 20 mg/dl of ascorbic acid is coexistent in Example 8 in which the copper ion, POD, phenol, and 4-AAP are coexistent, no influence is observed upon the values of the glucose, while even when 5 mg/dl of ascorbic acid is coexistent in Comparative Example 2, a negative influence appears.

As shown in FIG. 8, it is understood that the effect of removing the interference of ascorbic acid according to the method of the present invention is substantially equal to that in AOD.

Example 9

Measurement of Free Cholesterol (Two Liquid Method)

Measuring Reagent (1) First reagent liquid:
$CuSO_4 \cdot 5H_2O$, BSdiproPM, POD, uricase and Triton X-100 were dissolved into 0.05M phosphate buffer solution (pH=7.0) to be at concentrations of 0.01%, 0.1 m mol/l, 500 U/dl, 30 U/dl, and 0.1% respectively.

(2) Second reagent solution:
Cholesterol oxidase and Triton X-100 were dissolved into 0.05M phosphate buffer solution to be at concentrations of 0.20 U/dl, and 0.1% respectively.

Measuring Method

A serum solution in which ascorbic acid was added into 100 ml of serum to be at a concentration of 10, 20, 30, 40, 50 or 100 mg/dl was used.

10 μl of the sample solution was sampled, 1 ml of the first reagent solution was added thereto, and was incubated at 37° C. for 5 minutes. Then, 2 ml of the second reagent solution was added, and was incubated at 37° C. for 5 minutes. Thereafter, an absorbance at a wavelength of 620 nm was measured with reference to a reagent blank as a control. Measured results were shown in Table 9.

Comparative Example 3

Measuring Reagent (1) First reagent solution:
Same as the first reagent solution in Example 9 except for $CuSO_4 \cdot 5H_2O$ being excluded therefrom
(2) Second reagent solution:
Same as in Example 9

Measuring Method

Free cholesterol was measured by using the same sample solution as in Example 9 according to the measuring method in Example 9. Measured results were shown in Table 9.

Reference Example 3

Measuring Reagent (1) First reagent solution:
AOD, BSdiproPM, POD, uricase, and Triton X-100 were dissolved into 0.05M phosphate buffer solution (pH=7.0) to be at concentrations of 30 U/dl, 0.1 m mol/l, 500 U/dl, 30 U/dl and 0.1% respectively.
(2) Second reagent solution:
Same as in Example 9

Measuring Method

Free cholesterol was measured by using the same sample solution as in Example 9 according to the measuring method in Example 9. Measured results were shown in Table 9.

Example 10

Measurement of Free Cholesterol (One Liquid Method)

Measuring Reagent

A mixture of the first reagent solution and the second reagent solution in Example 9 at a mixing ratio of 1:2 was used.

Measuring Method

The same sample solution as in Example 9 was used.
10 μl of the sample solution was sampled, 3 ml of the measuring reagent was added, and was incubated at 37° C. for 10 minutes. Then, an absorbance at a wavelength of 620 nm was measured with reference to a reagent blank as a control. Measured results were shown in Table 9.

Comparative Example 4

Measuring Reagent

A mixture of the first reagent solution and the second reagent solution in Comparative Example 3 at a mixing ratio of 1:2 was used.

Measuring Method

Free cholesterol was measured by using the same sample solution as in Example 9 according to the measuring method in Example 10. Measured results were shown in Table 9.

Reference Example 4

Measuring Reagent

A mixture of the first reagent solution and the second reagent solution in Reference Example 3 at a mixing ratio of 1:2 was used.

Measuring Method

Free cholesterol was measured by using the same sample solution as in Example 9 according to the measuring method in Example 10. Measured results were shown in Table 9.

TABLE 9

| Added amount of ascorbic acid (mg/dl) | Absorbance (OD) | | | | | |
|---|---|---|---|---|---|---|
| | Two liquid method | | | One liquid method | | |
| | Example 9 ($Cu^{2+}$ contained) | Comparative Example 3 | Reference Example 3 (AOD contained) | Example 10 ($Cu^{2+}$ contained) | Comparative Example 4 | Reference Example 4 (AOD contained) |
| 0 | 0.568 | -0.559 | 0.571 | 0.560 | 0.563 | 0.570 |

TABLE 9-continued

| Added amount of ascorbic acid (mg/dl) | Absorbance (OD) | | | | | |
|---|---|---|---|---|---|---|
| | Two liquid method | | | One liquid method | | |
| | Example 9 ($Cu^{2+}$ contained) | Comparative Example 3 | Reference Example 3 (AOD contained) | Example 10 ($Cu^{2+}$ contained) | Comparative Example 4 | Reference Example 4 (AOD contained) |
| 10 | 0.569 | 0.478 | 0.568 | 0.481 | 0.451 | 0.501 |
| 20 | 0.568 | 0.376 | 0.561 | 0.414 | 0.330 | 0.426 |
| 30 | 0.568 | 0.202 | 0.573 | 0.384 | 0.165 | 0.412 |
| 40 | 0.561 | 0.078 | 0.562 | 0.351 | 0.051 | 0.370 |
| 50 | 0.567 | 0 | 0.554 | 0.329 | 0 | 0.363 |
| 100 | 0.562 | 0 | 0.536 | 0.313 | 0 | 0.342 |

As shown in Table 9, the effect of removing the interference of ascorbic acid according to the method of the present invention is equivalent to or more excellent than AOD with respect to the one liquid method and the two liquid method, and the influence of up to 100 mg/dl of ascorbic acid can be completely avoided in the case of the two liquid method.

Example 11

Measurement of Free Cholesterol (Two Liquid Method)

Measuring Reagent

Same as in Example 9

Measuring Method

A serum solution in which bilirubin was added to 100 ml of serum to be at a concentration of 0, 5, 10, 15 or 20 mg/dl was used as a sample solution.

10 μl of the sample solution was sampled, 1 ml of the first reagent solution was added, and was incubated at 37° C. for 5 minutes. Then, 2 ml of the second reagent solution was added, and was further incubated at 37° C. for 5 minutes. Thereafter, an absorbance at a wavelength of 620 nm was measured with reference to a reagent blank as a control. Measured results were shown in Table 10.

Comparative Example 5

Measuring Reagent

Same as in Comparative Example 3

Measuring Method

Free cholesterol was measured by using the same sample solution as in Example 11 according to the measuring method in Example 11. Measured results were shown in Table 10.

Reference Example 5

Measuring Reagent

Same as in Reference Example 3

Measuring Method

Free cholesterol was measured by using the same sample solution as in Example 11 according to the measuring method in Example 11. Measured results were shown in Table 10.

Example 12

Measurement of Free Cholesterol (One Liquid Method)

Measuring Reagent

Same as in Example 10

Measuring Method

The same sample solution as in Example 11 was used. 10 μl of the sample solution was sampled, 3 ml of the measuring reagent was added, and was incubated at 37° C. for 10 minutes. Then, an absorbance at a wavelength of 620 nm was measured with reference to a reagent blank as a control. Measured results were shown in Table 10.

Comparative Example 6

Measuring Reagent

Same as in Comparative Example 4

Measuring Method

Free cholesterol was measured by using the same sample solution as in Example 11 according to the measuring method in Example 12. Measuring results were shown in Table 10.

Reference Example 6

Measuring Reagent

Same as in Comparative Example 4

Measuring Method

Free cholesterol was measured by using the same sample solution as in Example 11 according to the measuring method in Example 12. Measured results were shown in Table 10.

TABLE 10

| Added amount of bilirubin (mg/dl) | Absorbance (OD) | | | | | |
|---|---|---|---|---|---|---|
| | Two liquid method | | | One liquid method | | |
| | Example 11 ($Cu^{2+}$ contained) | Comparative Example 5 | Reference Example 5 (AOD contained) | Example 12 ($Cu^{2+}$ contained) | Comparative Example 6 | Reference Example 6 (AOD contained) |
| 0 | 0.572 | 0.563 | 0.568 | 0.572 | 0.572 | 0.576 |
| 5 | 0.562 | 0.510 | 0.530 | 0.550 | 0.510 | 0.526 |
| 10 | 0.526 | 0.454 | 0.486 | 0.493 | 0.460 | 0.475 |
| 15 | 0.473 | 0.433 | 0.456 | 0.472 | 0.447 | 0.442 |
| 20 | 0.442 | 0.382 | 0.438 | 0.421 | 0.384 | 0.440 |

As shown in Table 10, the effect of removing the interference of bilirubin according to the method of the present invention is equivalent to or more excellent than AOD with respect to both the one liquid method and the two liquid method.

Example 13

Measuring Reagent $CuSO_4 \cdot 5H_2O$, ABTS, POD, cholesterol oxidase, and Triton X-100 were dissolved into 0.05M phosphate buffer solution (pH=7.0) to be at concentrations of 0.003%, 0.1%, 300 U/dl, 15 U/dl, and 0.1%.

Measuring Method

An aqueous solution containing 100 mg/dl of cholesterol and 0, 10, 20, 30, 40 or 50 mg/dl of ascorbic acid in 100 ml was used as a sample solution.

20 μl of the sample solution was sampled, 3 ml of the measuring reagent was added, and was incubated at 37° C. for 10 minutes. Then, an absorbance at a wavelength of 660 nm was measured with reference to a reagent blank as a control. Measured results were shown in Table 11.

Comparative Example 7

Measuring Reagent

Same as the measuring reagent in Example 13 except for $CuSO_4 \cdot 5H_2O$ being excluded therefrom

Measuring Method

Free cholesterol was measured by using the same sample solution as in Example 13 according to the measuring method in Example 13. Measured results were shown in Table 11.

TABLE 11

| Ascorbic acid concentration in the sample solution (mg/dl) | Absorbance (OD) | |
|---|---|---|
| | Example 13 | Comparative Example 7 |
| 0 | 0.216 (100) | 0.210 (100) |
| 10 | 0.174 (81) | 0.165 (79) |
| 20 | 0.135 (62) | 0.108 (51) |
| 30 | 0.116 (54) | 0.056 (27) |
| 40 | 0.107 (50) | 0 (0) |
| 50 | 0.087 (40) | 0 (0) |

Figures in the parentheses mean recovery rates (%) of cholesterol.

It is seen from Table 11 that the effect of removing the interference of ascorbic acid is obtained when the copper ion, POD and ABTS are coexistent.

INDUSTRIAL APPLICABILITY

The method according to the present invention can be used for effectively removing the adverse affect of ascorbic acid coexisting in the sample in the quantitative measurement of the intended component in the sample to be examined by utilizing the oxidation-reduction reaction.

What is claimed is:

1. The method for quantitatively measuring a selected component in a sample of body fluid wherein an adverse influence of a reducing substance is prevented, said method consisting essentially of:
providing a sample of a body fluid containing a reducing substance,
introducing into said sample, copper ions, peroxidase, and at least one compound selected from the group consisting of:
4-aminoantipyrine,
3-methyl-2-benzothiazolinonehydrazone,
2,2'-azinobis(3-ethylbenzothiazoline-6-sulfonic acid,
leucomalachite green, leucocrystal violet, bis(p-diethylaminophenyl)-2-sulfophenylmethane, bis(p-diethylamino-phenyl)-4-sulfopropoxyphenyl methane sodium salt, bis(p-diethylaminophenyl)-3,4-disulfopropoxyphenyl methane disodium salt,
phenol compounds,
aniline compounds,
naphthol compounds, and
mixtures thereof;
and enzymatically producing hydrogen peroxide in said sample by the action of an enzyme action upon a substrate; and
quantifying the thus produced hydrogen peroxide.

2. The method according to claim 1, wherein the reducing substance is ascorbic acid.

3. The method according to claim 2, wherein the reducing substance is bilirubin.

4. A method for quantitatively measuring the amount of a selected component in a sample of body fluid containing ascorbic acid, removing the influence of ascorbic acid, said method consisting essentially of the following steps:
decomposing the ascorbic acid contained in a sample into products of water and dehydroascorbic acid by adding, concurrently, thereto copper ion, peroxidase and at least one compound selected from the group consisting of:
4-aminoantipyrine,
3-methyl-2-benzothiazolinonehydrazone,
2,2'-azinobis(3-ethylbenzothiazoline-6-sulfonic acid),
leucomalachite green, leucocrystal violet,
bis(p-diethylaminophenyl)-2-sulfophenyl methane,
bis(p-diethylamino-phenyl)-4-sulfopropoxyphenyl methane sodium salt,
bis(p-diethyl-aminophenyl)-3,4-disulfopropoxyphenyl methane disodium salt,
phenol compounds,
aniline compounds,
naphthol compounds, and
mixtures thereof; and
quantifying the amount of said selected component in said sample following an oxidation-reduction reaction of said component.

5. A method for quantitatively measuring the amount of a selected component in a sample of body fluid containing ascorbic acid, removing the influence of ascorbic acid, said method comprising the following steps:
decomposing the ascorbic acid contained in a sample into products of water and dehydroascorbic acid by adding, concurrently, thereto copper ion, peroxidase and at least one compound selected from the group consisting of:
4-aminoantipyrine,
3-methyl-2-benzothiazolinonehydrazone,
2,2'-azinobis(3-ethylbenzothiazoline-6-sulfonic acid),
leucomalachite green, leucocrystal violet,
bis(p-diethylaminophenyl)-2-sulfophenyl methane,
bis(p-diethylamino-phenyl)-4-sulfopropoxyphenyl methane sodium salt,
bis(p-diethyl-aminophenyl)-3,4-disulfopropoxyphenyl methane disodium salt,
phenol compounds, aniline compounds,
naphthol compounds, and
mixtures thereof; and
quantifying the amount of said selected component in said sample following an oxidation-reduction reaction of said component.

6. The method according to claim 5, wherein the oxidation-reduction reaction is an enzyme reaction, the component is a substrate, and said enzyme is an oxidase capable of acting on said substrate to produce $H_2O_2$.

7. The method according to claim 6, wherein in said method:
said substrate is selected from the group consisting of
glucose, cholesterol, glycerol, glycerol phosphate, choline, acylCoA, pyruvic acid, uric acid, xanthine and lactic acid; and
the oxidase is selected from the group consisting of
glucose oxidase, cholesterol oxidase, glycerol oxidase, glycerol phosphate oxidase, choline oxidase, acylCoA oxidase, pyruvante oxidase, uricase, xanthine oxidase and lactate oxidase.

8. The method according to claim 7, wherein said quantifying of the amount of said component in the body fluid is conducted by colorimetrically, quantitatively measuring a color developed through oxidization of an oxidizable coloring reagent in the presence of peroxidase and $H_2O_2$ produced by action of the oxidase.

9. The method according to claim 8, wherein decomposing the ascorbic acid and subjecting said sample to the enzyme reaction for evaluation in a quantitative colormetric determination step are conducted in one step.

* * * * *